United States Patent [19]
Gavach et al.

[11] Patent Number: 5,993,629
[45] Date of Patent: *Nov. 30, 1999

[54] REGENERATING OF ACIDS, PARTICULARLY OF STRONG ORGANIC ACIDS, USING BIPOLAR MEMBRANES

[75] Inventors: Claude Gavach, Saint-Jean-De-Vedas; Christian Gancet, Lons; Alfred Mirassou, Poey; Frederic Perie, Billere, all of France

[73] Assignee: Elf Atochem S.A., France

[ * ] Notice: This patent issued on a continued prosecution application filed under 37 CFR 1.53(d), and is subject to the twenty year patent term provisions of 35 U.S.C. 154(a)(2).

[21] Appl. No.: 08/875,072
[22] PCT Filed: Jan. 11, 1996
[86] PCT No.: PCT/FR96/00042
  § 371 Date: Jul. 17, 1997
  § 102(e) Date: Jul. 17, 1997
[87] PCT Pub. No.: WO96/22154
  PCT Pub. Date: Jul. 25, 1996

[30] Foreign Application Priority Data

Jan. 18, 1996 [FR] France .................. 95/00499

[51] Int. Cl.⁶ .................. B01D 61/44
[52] U.S. Cl. .................. 204/534; 204/537; 204/539; 204/631
[58] Field of Search .................. 204/534, 539, 204/631, 537

[56] References Cited

U.S. PATENT DOCUMENTS

| | | | |
|---|---|---|---|
| 5,126,026 | 6/1992 | Chlanda | 204/534 |
| 5,135,626 | 8/1992 | Mani et al. | 204/182.4 |
| 5,221,443 | 6/1993 | Voss et al. | 204/131 |
| 5,288,378 | 2/1994 | Chlanda | 204/531 |

FOREIGN PATENT DOCUMENTS

| | | |
|---|---|---|
| 439636 | 7/1991 | European Pat. Off. . |
| 492209 | 7/1992 | European Pat. Off. . |
| 2646421 | 11/1990 | France . |
| 4-132605 | 5/1992 | Japan . |
| WO 88/07975 | 10/1988 | WIPO . |
| WO 90/06167 | 6/1990 | WIPO . |

OTHER PUBLICATIONS

Chemical Abstracts 117:153850m "Use of bipolar membranes for ion exchange resin regenerant production", H. R. Bolton, J. Chem. Technol. Biotechnol. 1992, 54(4), 341–7.

Chemical Abstracts, vol. 109, p. 320, 115424u "On–site generation of acid and base with bipolar membranes: a new alternative to purchasing and storing regenerants", Davis, et al, Proc. —Int. Water Conf. Eng. Soc. West. Pa. 1987 48th 316–23.

(List continued on next page.)

*Primary Examiner*—Arun S. Phasge
*Attorney, Agent, or Firm*—Bell, Boyd & Lloyd

[57] ABSTRACT

An electrodialysis method using a bipolar membrane (BP) for regenerating acids, wherein a series of base (B), acid (A) and salt (S) compartments are provided between a positive electrode (anode) and a negative electrode (cathode), said compartments being defined by a series of membranes: cationic, bipolar, anionic, cationic, bipolar and so forth, and a solution being circulated through each compartment. An additional anionic membrane (10) is applied to the anionic side (11) of the bipolar membrane (BP) with no discernible gap therebetween so that contamination of the acid compartment by cations is reduced.

10 Claims, 4 Drawing Sheets

OTHER PUBLICATIONS

Chemical Abstracts, vol. 92, 1980 p. 116, 43961f "Production of caustic soda amd hydrochloric acid from sea water by electrodialysis with bipolar membranes, Part 1. Current efficiency of acid and alkali." V. Greben, et al.

Chemical Abstracts, vol. 92, p. 168, 25083s Production of caustic soda and hydrochloric acid from sea water by electro dialysis with bipolar membranes, Part 2. Voltage drop across the membranes. V. Greben 1980.

Chemical Abstracts, vol. 116, p. 529, 182124n "Conversion of sodium butyrate in electrodialysis with bipolar membranes", Krasova, et al. 1991.

Chemical Abstracts, vol. 107 p. 419, 29755p Electrodialysis method with bipolar membranes for the regeneration of boric acid from a spent coolant, Dudnik, et al. 1985.

Chemical Abstracts, vol. 114, p. 431, 30673m "Electrodialysis of boron–containing solutions with the use of a bipolar membrane MB–2" Pilipenko, et al. 1990.

Organic Analytical Chemistry, vol. 71, p. 533, 5644f "Thin–layer chromatography for identification of isomeric ketones", Zalesskaya, et al. 1968.

REGENERATING OF ACIDS, PARTICULARLY OF STRONG ORGANIC ACIDS, USING BIPOLAR MEMBRANES

FIELD OF THE INVENTION

The present invention relates to the field of electrodialysis and the subject of the invention is more particularly the regeneration of strong organic acids by electrodialysis using bipolar membranes.

BACKGROUND OF THE INVENTION

Acids and bases are important intermediates in the manufacture of a large number of chemicals. After they have been used, these acids and these bases generally are in the form of saline aqueous solutions from which it is necessary to strip them. For environmental and economic reasons, it is desirable to regenerate the initial acids and bases directly from the salts contained in these industrial effluents.

Electrodialysis using bipolar membranes enables such regeneration to be carried out. This known method uses electrical energy to dissociate the water of the saline solution and to recover the acid and the base separately according to the reaction:

$$MX + H_2O \longrightarrow HX + MOH$$
$$\text{salt} \qquad\qquad \text{acid} \quad \text{base}$$

In order to carry out this reaction and to keep the species separate, ion-exchange membranes and, more particularly bipolar membranes consisting of two faces, respectively selective to the anions and to the cations, are used. Under the influence of an electric field, these membranes allow the following reaction:

$$H_2O \rightarrow H^+ + OH^-$$

The $H^+ + OH^-$ ions are then recombined respectively with the anions $X^-$ and cations $M^+$ coming from the salt, and the species obtained are kept separate by conventional (monopolar) ion-exchange membranes in a three-compartment cell.

This method of regeneration from salts into acids and into bases has already been applied to many cases, for example:

sulfuric acid from $Na_2SO_4$ (the Patent Publication JP-4-132605 and the article by S. SRIDHAR "Elektrodialyse mit bipolaren Membranen [*Electrodialysis using bipolar membranhes*]" in Chem. Ing. Tech. 61 (1989) No. 5, pp. 428–429);

hydrochloric acid from NaCl [abstracts Chemical Abstracts 117(16): 153850m, 109(2): 11524u, 92(6): 43961f and 92(4): 25083s];

butyric acid from its sodium salt [abstract CA 116(18): 182124n];

maleic acid from its ammonium salt (the aforementioned article by S. SRIDHAR);

boric acid from borates [abstracts CA 107(4): 29755p and CA 114(4): 30673m];

tartric acid from its potassium salt (Patent Application FR 2,646,421);

organic sulfonic acids [abstract CA 71(12) 56451f and U.S. Pat. No. 5,221,443].

The bipolar membranes currently available on the market exhibit performance characteristics which vary depending on the technology used to manufacture them and depending on the supplier. Owing to their nature, bipolar membranes are in principle nonpermeable to cations and to anions which are respectively stopped by the anionic and cationic layers of the bipolar membrane.

DESCRIPTION OF THE INVENTION

The inventors have observed that, during the regeneration of strong organic acids from their salts, by electrodialysis using bipolar membranes, there was contamination of the acid obtained from the cation of the salt, in particular from sodium. This contamination, which varies depending on the level of concentration of the base chosen for working with, is highly problematic when it is desired to obtain an acid of high purity. Thus, in order to regenerate methanesulfonic acid (MSA) from aqueous solutions of mesylates, this contamination constitutes a very considerable obstacle when MSA has subsequently to be concentrated to a high level; the salt present in the acid also concentrates and, for a certain value of concentration, an MSA/salt of MSA/water ternary mixture precipitates and sets solid.

The inventors have determined that the contamination of the acid with alkaline cation comes from the base compartment, which is separated from the acid compartment by the bipolar membrane, and not from the salt compartment, which is separated from the acid compartment by a monopolar anionic membrane.

The inventors have thus found that in fact the bipolar membranes used hitherto exhibit cation leakage, in particular sodium leakage, causing contamination of the acid during the regeneration operation.

The inventors have then found that the permeability of the bipolar membranes to cations, in particular sodium, may be considerably reduced, without a substantial contrary effect on the electrodialysis process, by adding an anionic membrane on the anionic face of the bipolar membranes. The anion-exchange membranes have a very low transport number for cations and consequently constitute very effective barriers for limiting their diffusion. Joining together an anionic membrane A,10 and a bipolar membrane BP, as shown diagrammatically in FIG. 1, functions as an electrodialysis cell having several bipolar membranes.

The subject of the invention is therefore a method of regenerating acids, in particular strong organic acids, from their salts, by electrodialysis using a bipolar membrane, characterized in that at least one additional anionic membrane is applied against the anionic face, delimiting a base compartment, of the bipolar membrane so as to reduce the contamination of the acid compartment, lying on the other side of the bipolar membrane, with cations.

Sealing is provided around the entire perimeter between the anionic membrane and the bipolar membrane.

As anionic membrane, it is possible to use any commercial anionic membrane, for example those sold by Asahi Glass under the name SELEMION®, by Tokuyama Soda under the name NEOSEPTAE® or by Solvay. These commercial membranes generally have a thickness of between 0.1 and 1 mm and a pore diameter of between 1 and 30 $\mu m$. The anion-exchange membranes are normally composed of a polymeric matrix, such as divinylbenzene-polystyrene, containing chemically bound cationic groups (for example ammonium or substituted ammonium), while the cationic-exchange membranes contain carboxylate or sulfonate groups.

Although the process according to the invention is aimed more particularly at the regeneration of methanesulfonic acid from its alkaline salts, in particular from the sodium salt, it may be applied generally to the regeneration of strong organic acids such as sulfonic acids and phosphonic acids, provided that their molecular mass is not too great.

The electrodialysis proper is carried out under the normal conditions known to those skilled in the art.

The invention also relates to an electrodialysis device, using a bipolar membrane for implementation of the process, consisting of a stack of cationic, bipolar and anionic membranes, with interposition of elements, between two clamping plates applied against electrode supports and characterized in that it includes, at each bipolar membrane, an additional anionic membrane applied against the anionic face of the bipolar membrane, this additional anionic membrane and the bipolar membrane being clamped in a sealed manner, around their entire perimeter, between two frame gaskets in such a way that no measurable space remains between the contacting faces of the additional anionic membrane and of the bipolar membrane.

Preferably, all the elements of the stack, including the bipolar membrane and the additional anionic membrane, have the same outer profiles and include, on their periphery, holes for fluid flow.

The invention will be more clearly understood with the aid of embodiment examples which are described with reference to the drawings appended hereto but which are in no way limiting.

BRIEF DESCRIPTION OF THE DRAWINGS

Of these drawings.

Finally.

Referring to the drawings, it may be seen that, according to the invention, an anionic membrane A,10 (or simply 10) is joined to a bipolar membrane BP by being intimately applied against the anionic face of the bipolar membrane BP. In FIG. 1, a gap has been shown between the anionic membrane A,10 and the anionic face of the bipolar membrane BP in order to show that the anionic membrane A,10 is an additional membrane which has been added. In reality, there is no space between this added anionic membrane and the bipolar membrane. The anionic membrane A,10 is applied intimately against the anionic face of the bipolar membrane BP and there is no fluid flow between these membranes parallel to their mid-plane, unlike what occurs in the various compartments of an electrodialysis cell.

Before describing in more detail the additional anionic membrane joined to the bipolar membrane, with reference to FIGS. 4 to 7, a number of examples will be considered.

EXAMPLES

The following examples, which illustrate the invention without limiting it, were produced in a conventional-type device comprising three circuits for the reactants (salt, acid and base) and one circuit for the electrolyte (2.5N NaOH).

Figure 1:
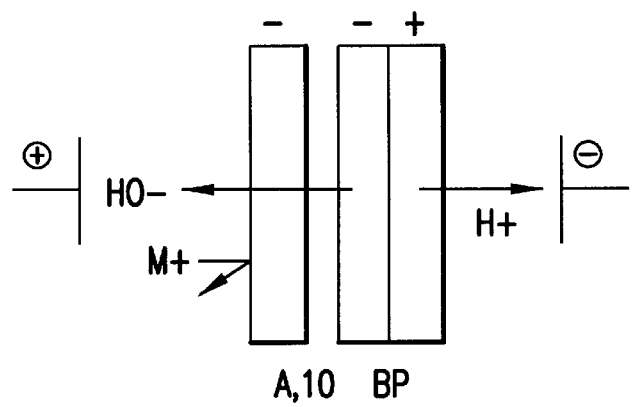
FIG. 1 is a diagram of an anionic membrane joined to a bipolar membrane, according to the invention, in which diagram the anionic membrane has been represented, for the purpose of explanation, away from the anionic face of the bipolar membrane, whereas in reality the anionic membrane is pressed against this anionic face.
Figure 2:
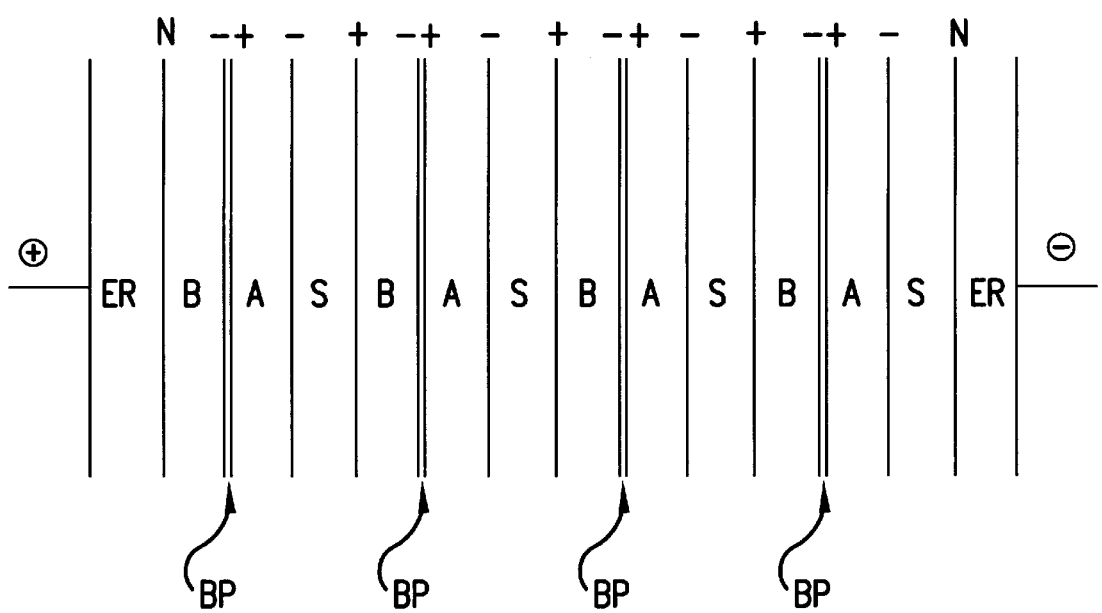
FIG. 2 is a simplified diagram of electrodialysis cells of a known type.

The volume of the reservoir of each circuit was approximately 8 liters and the structure of the stack used, shown diagrammatically in FIG. 2 in which the symbols and letters have the following meanings:

−+ bipolar membrane
− anionic membrane
+ cationic membrane
N Nafion (cationic) membrane
S salt compartment
A acid compartment
B base compartment
ER electrode rinsing, corresponded to 4 cells for a total surface area of 0.04 m$^2$.

The general parameters used were as follows:
maximum voltage (for this stack): 20 volts
maximum current (for this stack): 10 amps
flow rate of the electrolyte (per electrode): 50 l/h
flow rate of each reactant: 90 l/h
pressure on the input side of the stack: 0.4–0.5 bar.

Example 1 (Comparative)

By way of comparison, a first treatment by electrodialysis of an MSA solution using a bipolar membrane was made using conventional electrodialysis cells illustrated in FIG. 2. The acid compartment A is delimited, on one side, by the cationic face of a conventional bipolar membrane BP and, on the other side, by an anionic monopolar membrane. On the other side of the bipolar membrane BP is the base compartment B which is therefore delimited by the anionic face of the bipolar membrane and by a cationic monopolar membrane. On the other side of the anionic membrane delimiting the acid compartment A is the salt compartment S delimited by a cationic membrane establishing separation between the salt compartment S and the base compartment B. The gaps between the membranes in a direction perpendicular to their mid-plane are sufficient to allow liquid to flow through the compartments in question.

The device according to the diagram in FIG. 2 was equipped with 4 WSI bipolar membranes supplied by WSI Technologies Inc., 5 cationic membranes (2 Nafion membranes from DuPont de Nemours and 3 CMV membranes from Asahi Glass) and 4 AAV anionic membranes from Asahi Glass.

The salt compartment was charged with 4 liters of a sodium mesylate solution to be regenerated (210 g/l and a pH of 3.0) and the acid and base compartments were charged respectively with 3 liters of a 0.56 N solution of MSA containing 150 ppm of Na$^+$ and 3 liters of a 0.53 N sodium hydroxide solution.

The flow rates were fixed at 90 l/h, the current at 10 A and the voltage adjusted between 16 and 20 V in order to obtain this current.

After operating for 5 hours, the concentration of the MSA solution had risen to 1.62 N for a final volume of 3.5 liters, and that of the NaOH solution to 2.16 N. During this period of operation, the sodium content in the MSA solution went from 150 to 1000 ppm, which corresponds to the diffusion of 3025 mg of sodium during the period of the test.

EXPERIMENT SHOWING THE SOURCE OF THE SODIUM PRESENT IN THE MSA.

After having observed the contamination of the acid by sodium, according to this Example 1, the inventors endeavored to determine the cause of it.

The following experiment was carried out.

Repeating the conditions in Example 1, an NaMS (sodium mesylate) solution was made to flow through the salt compartment S, while, instead of sodium hydroxide, a potassium hydroxide KOH solution was made to flow through the base compartment B.

With no electric current, the diffusion of the cations into the acid compartment A was monitored. At time t=0, the respective concentrations in the MSA of the acid compartment A was 106 ppm in the case of $Na^+$ and 1 ppm in the case of $K^+$.

After the solutions had flowed through the compartments for five hours, the concentrations in the acid compartment A had become, respectively, 107 ppm in the case of $Na^+$ and 129 ppm in the case of $K^+$.

In other words, the concentration of $Na^+$ cations in the acid compartment A practically did not vary, and these cations, which can only come from the salt compartment S, therefore did not pass through the cationic monopolar membrane separating the acid compartment from the salt compartment.

On the other hand, the concentration of $K^+$ cations in the acid compartment A had increased considerably. These $K^+$ cations can only come from the base compartment B separated from the acid compartment by the bipolar membrane BP.

This experiment therefore shows that the contamination of the acid compartment A with alkaline cations is due to a certain permeability of the bipolar membrane BP with respect to this alkaline cation.

Figure 3:
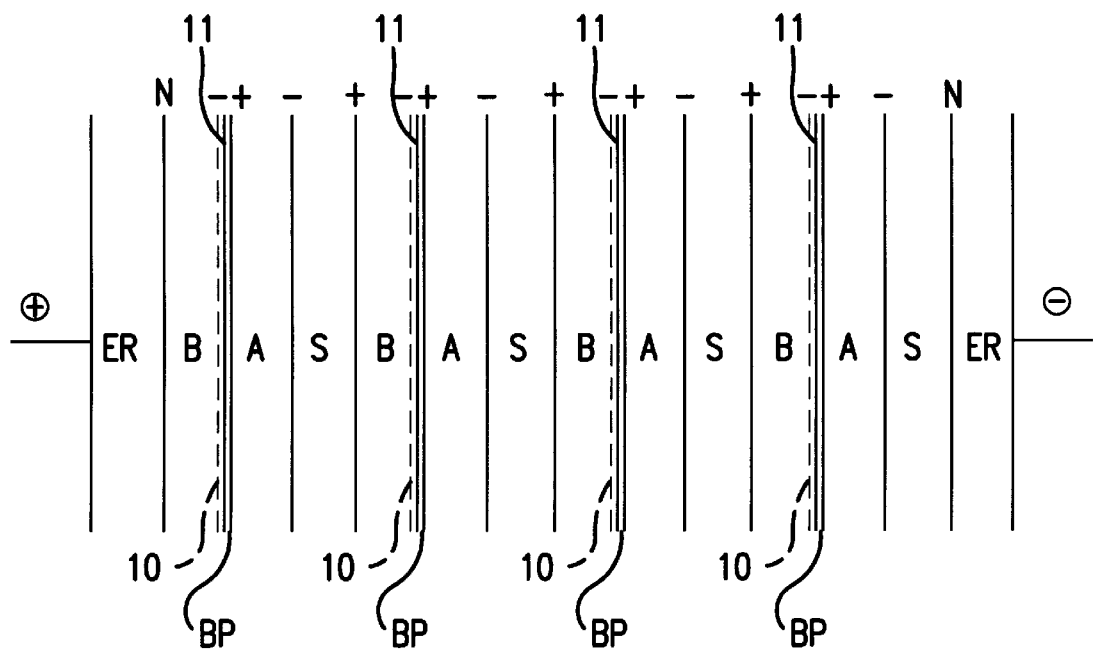
FIG. 3 is a diagram, similar to that in FIG. 2, of electrodialysis cells according to the invention.

Having thus found the source of the contamination, the inventors conceived a way of enhancing the impermeability of the bipolar membrane BP to the cations by applying an additional anionic membrane against the anionic face of the bipolar membrane BP, as illustrated in FIG. 3.

The diagram in FIG. 3, which is that of electrodialysis cells according to the invention, corresponds in its entirety to the conventional diagram in FIG. 2, the main difference being an additional anionic membrane 10 placed against the anionic face of each bipolar membrane BP.

Sealing is achieved around the entire outline of the membranes BP and 10, which are applied against each other; there is no flow of liquid between these membranes.

The experiments described in Examples 2 and 3 which follow were then carried out under the conditions specified below.

Example 2

The same device was used as in Example 1, but by applying (FIG. 3) an AMV anionic membrane 10 from Asahi Glass on the anionic face of each of the 4 bipolar membranes.

The salt compartment was charged with 4 liters of a sodium mesylate solution (210 g/l at a pH of 2.9) and the acid and base compartments were charged respectively with 3 liters of a 0.7N MSA solution containing 73 ppm of $Na^+$ and 3 liters of a 0.5N NaOH solution.

For an applied voltage of 20 V, the current observed was between 9 and 10 A. After operating for 5 hours, the concentration of the MSA solution had risen to 1.75N for a final volume of 3.4 liters and that of the NaOH solution to 1.73N. Over the same time, the sodium content in the MSA went from 73 to 316 ppm, which corresponds to the diffusion of 852 mg of sodium.

Compared with Example 1, a much lower diffusion of $Na^+$ cations was observed (a reduction by a factor of greater than 3).

Example 3

The same procedure as in Example 2 was carried out, but the AMV membranes used for reinforcing the anionic layer of the bipolar membranes were replaced by ADP anionic membranes from Solvay.

The MSA and NaOH concentrations were, at the start, respectively 0.58N and 0.57N and, after operating for 5 hours at a voltage of 20 V, 1.46N and 1.62N, the observed average current being 6–8 A. The final volume of MSA was 3.3 liters.

During the test, the sodium content of the MSA went from 56 to 123 ppm, which corresponds to the diffusion of 218 mg of sodium in 5 hours. This is approximately 4 times lower than in Example 2 and almost 14 times lower than in Example 1.

The following table recapitulates all the results from Examples 1 to 3.

| Example | Device | $Na^+$ leakage in 5 h (mg) | MSA production in 5 h (mol) | Na/MSA (mg/mol) |
|---|---|---|---|---|
| 1 | WSI bipolar membranes alone | 3025 | 4.0 | 756 |
| 2 | WSI membranes + AMV anionic membranes pressed against the anionic face of the bipolars | 852 | 3.8 | 224 |
| 3 | WSI membranes + ADP anionic membranes pressed against the anionic face of the bipolars | 218 | 3.1 | 70 |

For a more detailed description of the membranes used in the above examples, reference may be made to Volume 1 "Membranes d'électrodialyse" [*Electrodialysis membranes*]" of the work entitled "MEMBRANES SEMI-PERMEABLES CHARGEES ET SEPARATEURS ELECTROCHIMIQUES [*CHARGED SEMIPERMEABLE MEMBRANES AND ELECTROCHEMICAL SEPARATORS*]", published in 1991 by EDF (Les Renardiéres, BP 1, 77250 MORET-SUR-LOING). The reference assigned in this work to the various membranes is indicated in the following table:

| Membranes | References |
|---|---|
| AAV | ED A-07 |
| AMV | ED A-15 |
| ADP | ED M-11 |
| CMV | ED A-27 |
| Nafion | SD D-33 |
| WSI | ED W-01 |

A device for implementation of the process of the invention can be seen by referring to FIGS. 4 to 7.

Figure 4:
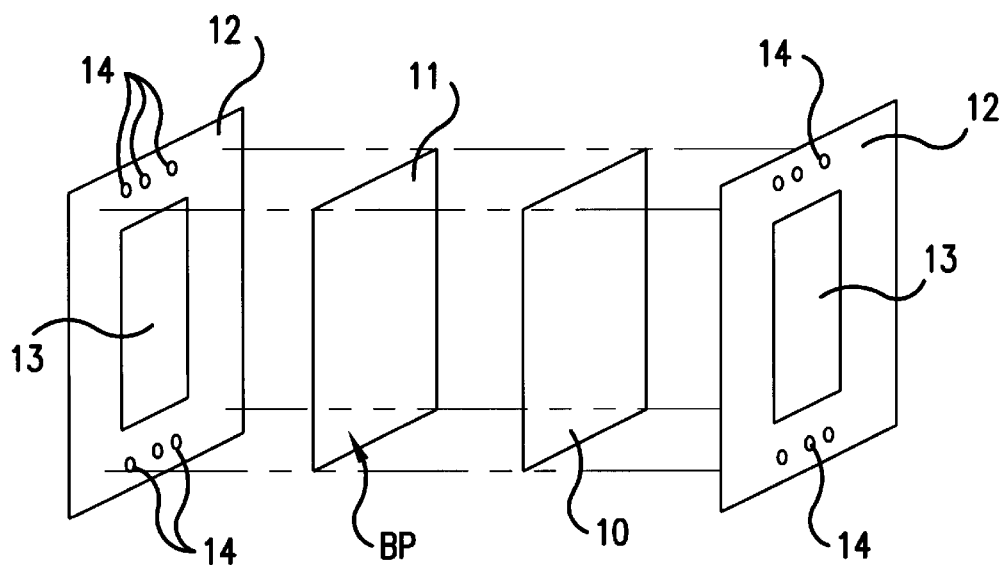
FIG. 4 is a simplified diagram, in perspective, of a bipolar membrane and an anionic membrane which are mounted, according to the invention, between two frame gaskets.

FIG. 4 shows diagrammatically the preparation of a bipolar membrane BP, the anionic face 11 of which is reinforced by an anionic membrane 10 according to the invention. As results from FIG. 4, the additional anionic membrane 10 is applied against the anionic face 11, without leaving a measurable space between the two contacting faces. The bipolar membrane BP and the associated additional anionic membrane 10, of rectangular shape in the example shown, are clamped, around their entire perimeter, between two frame gaskets 12 which are similar to those of the membranes and including a central opening 13, which is also rectangular. This opening 13 exposes a major part of that face of the membrane 10 which lies on the opposite side to the bipolar membrane BP, and of the cationic face of this membrane BP. The closed profile of the frame gaskets 12 includes several holes 14 for fluid flow, these being separated from each other. Stacking the holes in several elements makes it possible to create fluid-flow channels isolated from each other.

In the simplified example in FIG. 4, the bipolar membrane BP and the anionic monopolar membrane 10 have been shown with a profile having smaller dimensions than that of the frame gaskets 12, so that these membranes do not have fluid-flow holes similar to the holes 14.

Figure 5:
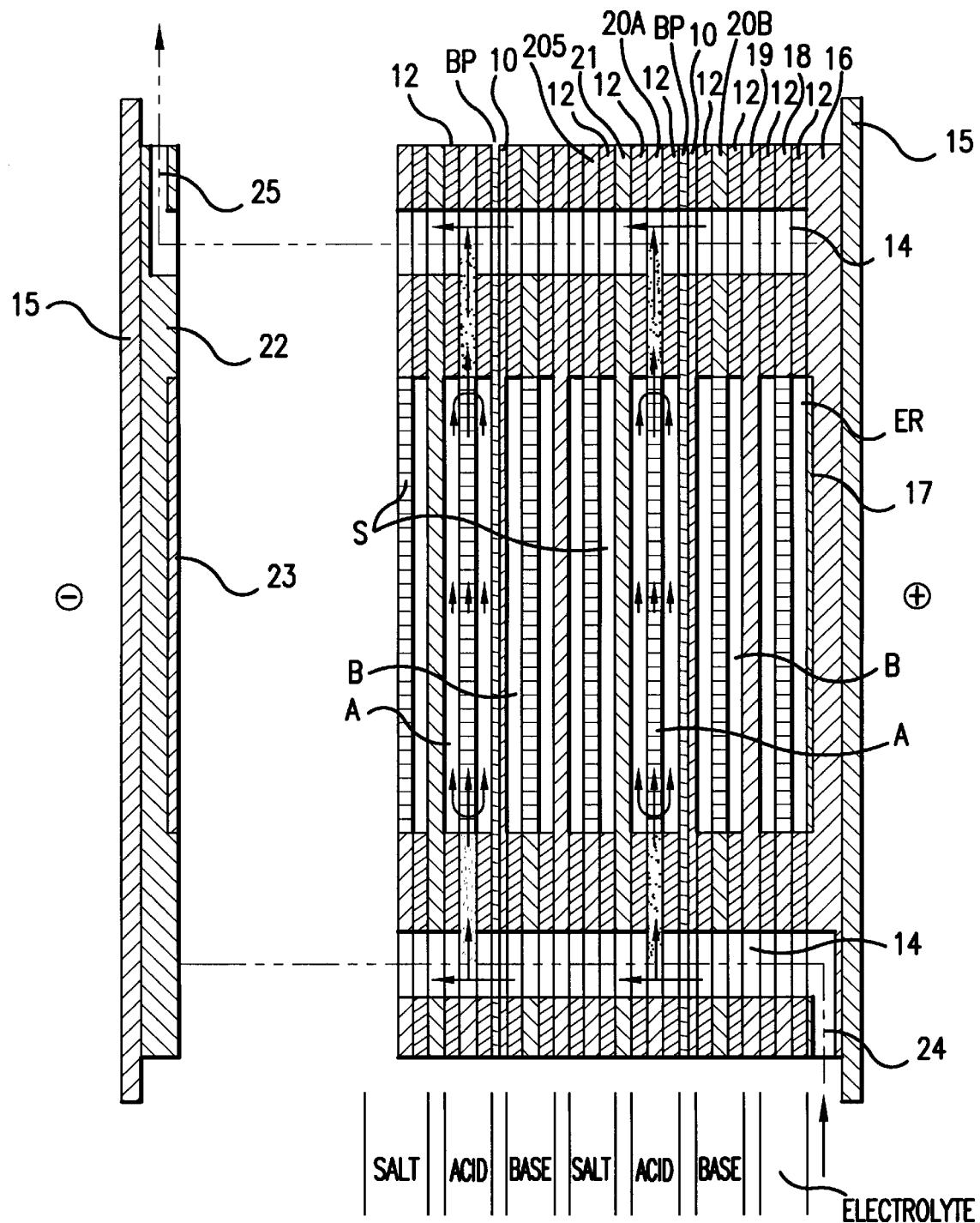
FIG. 5 is a section through a stack of compartments forming two cells.

However, as shown in the embodiment in FIG. 5, the membranes BP and 10 may have external dimensions identical to those of the frame gaskets 12 and include holes similar to the holes 14 which are aligned with those in the frame gaskets 12 and those in the other elements of the stack.

This stack in FIG. 5 comprises, from right to left: a clamping plate 15; an electrode support 16; an electrode, namely an anode, 17 housed in the electrode support 16; a first frame gasket 12 applied against the electrode support 16; an electrode separator 18; again, a frame gasket 12; a cationic membrane 19; a frame gasket 12; a compartment separator 20B, corresponding to the base compartment; a frame gasket 12; the additional anionic membrane 10 applied against the anionic face of the bipolar membrane BP; a frame gasket 12; a compartment separator 20A corresponding to the acid compartment; a frame gasket 12; a monopolar anionic membrane 21; a frame gasket 12; a compartment separator 20S corresponding to the salt compartment; a frame gasket 12; and, again, a cationic membrane 19. Thereafter, the succession of elements indicated above is repeated, making it possible to form a base compartment followed by an acid compartment and a salt compartment.

An electrodialysis cell corresponds to the combination of the three salt, base and acid compartments.

At the end of the stack on the left, there is an electrode support 22 in which the other electrode, namely the cathode 23, is housed. Another clamping plate 15 is applied against the electrode support 22, on the side opposite the stack.

All the sheet-like elements of the stack all have an identical rectangular outer profile and include holes 14 distributed around their periphery, at the same places, in order to form flow channels.

The electrode support 16 and the electrode support 22 are provided with ducts such as 24, 25 suitable for communicating with a channel formed by a stack of holes 14. The duct 24 constitutes the inlet for an acid to be regenerated in the example in question, while the duct 25 allows the regenerated acid to leave.

Figure 6:
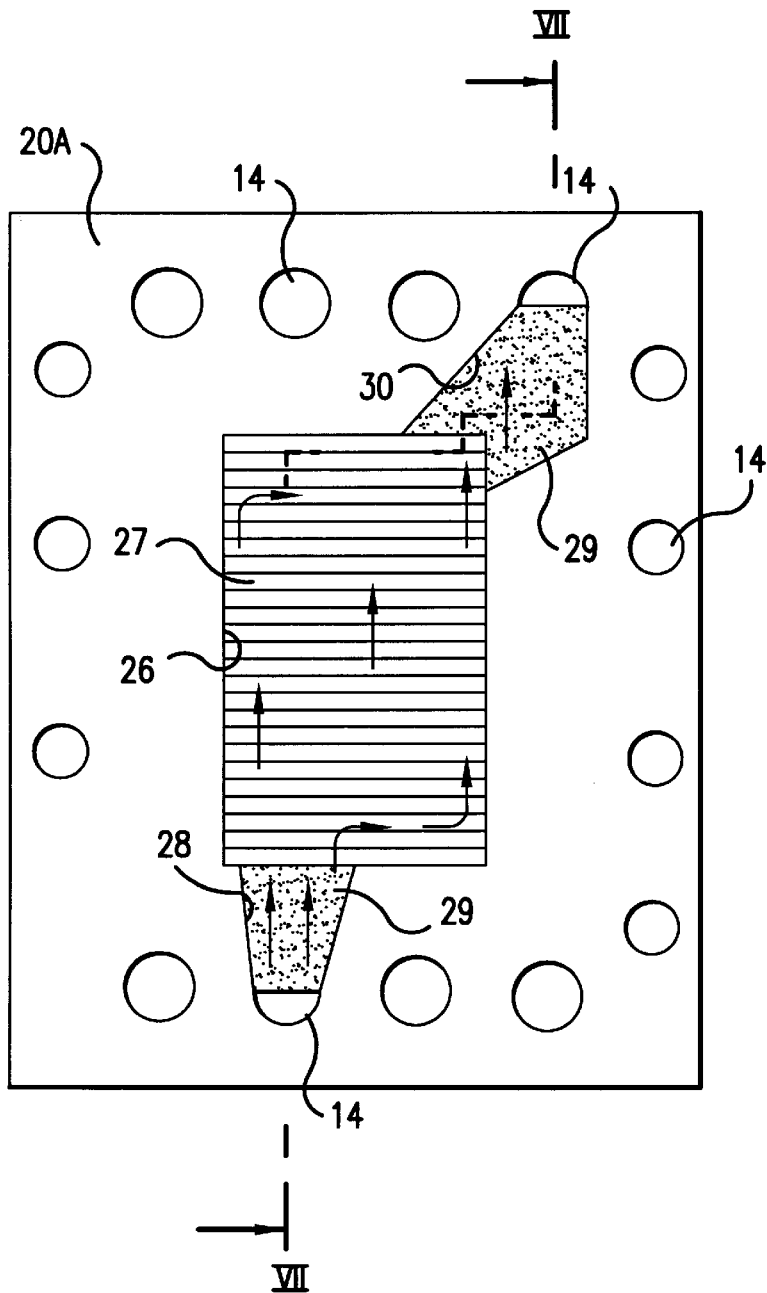
FIG. 6 is a front view of a compartment separator.
Figure 7:
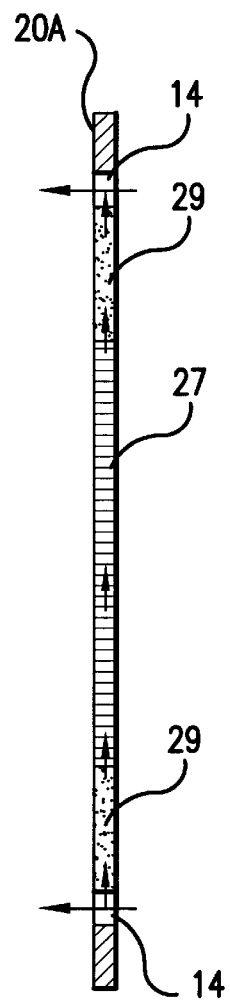
FIG. 7 is a section on the line VII—VII in FIG. 6.

As may be seen in FIG. 6, each compartment separator element, for example the element 20A in the case of the acid compartment, is formed by a plate, of defined thickness, having at the center a rectangular opening 26 provided with a mesh 27 allowing diffusion of the liquid without preventing its flow. The opening 26 is connected, for example along a segment of its edge, to a hole 14 via a hollowed part 28, having a trapezoidal profile, produced in the thickness of the sheet forming the element 20A. This hollowed part 28 includes a membrane 29 having internal channels for the flow of the fluid.

Another region of the profile of the opening 26, for example its top right corner in FIG. 6, is connected, via another hollowed part 30 of the separator element 20A, to a hole 14 serving for discharge of the liquid. The hollowed part 30 also includes a membrane 29 having internal channels for the flow of the liquid.

It may thus be seen that, by choosing the position of the hollowed parts 28, 30, it is possible to bring the chamber corresponding to the opening 27 into communication with different holes 14 and therefore with different channels. Thus, it is possible to produce a circuit for the acid using elements such as 20A, whereas, in respect of the salt, the elements 20S have hollowed parts which are placed differently, as is the case for the elements 20B relating to the base compartment.

As may be seen in FIG. 5, in an acid compartment, lying between the cationic face of the bipolar membrane BP and the anionic monopolar membrane 21, the length of the chamber along the direction of the axis of the stack is equal to the sum of two thicknesses of the frame gasket 12 and the thickness of the separator element 20A.

The inflow of the acid to be regenerated and its outflow can only take place via the multichannel membranes 29 lying in the hollowed regions 28 and 30 of the separator element 20A, between the frame gaskets 12. The arrows drawn in FIG. 5 enable the flow of the acid to be followed.

A similar flow takes place for the salt and the base in different channels.

Contrary to the case of the acid, base and salt compartments in which there is a non-negligible distance between the faces of the facing membranes delimiting these compartments, it may be seen that there is no space between the anionic face of the bipolar membrane BP and the additional anionic membrane 10. These two membranes are applied in a sealed manner around their perimeter depending on the pressure applied to the entire stack by the clamping of the electrode supports 15.

The mounting of the additional anionic membrane 10, achieved by cladding, constitutes a simple and economical way of enhancing the barrier effect in respect of the cations at the bipolar membrane and of considerably reducing contamination of the regenerated acid by the cations.

As already indicated, any anionic (anion-exchange) membrane may be suitable for this enhancement of the barrier effect. However, a membrane having a higher degree of crosslinking, such as ADP, gives better results than a standard anionic membrane, such as AMV.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are incorporated by reference.

We claim:

1. An electrodialysis process for the regeneration of strong organic acids from salts thereof with reduced salt cation contamination in the acid compartment, said process comprising the steps of:

supplying a strong organic acid solution selected from the group consisting of sulfonic acids and phosbonic acide to an electrodialysis device including a plurality of a repeating series of a base compartment, an acid compartment and a salt compartment between a positive electrode and a negative electrode;

each base compartment being defined by a first cationic membrane and an anionic face of a first bipolar membrane, each acid compartment being defined by a cationic face of the first bipolar membrane and a first anionic membrane, and each salt compartment being defined by the first anionic membrane and a second cationic membrane;

applying at least one additional anionic membrane against the anionic face of the first bipolar membrane in the base compartment for enhancing the impermeability of the first bipolar membrane to salt cation impurities from the base compartment and reducing salt cation contamination in the acid compartment, said additional anionic membrane being applied against the anionic face of the first bipolar membrane without leaving a measurable gap therebetween; and flowing the strong acid solution through the electrodialysis device to remove salts therefrom.

2. The process of claim 1 wherein an additional anionic membrane is applied against the anionic face of each one of the bipolar membranes in the repeating series for enhancing the impermeability of each one of the bipolar membranes to salt cation impurities from the respective base compartment and reducing salt cation contamination in the respective acid compartment.

3. The process of claim 1 wherein sealing is provided between the additional anionic membrane and the bipolar membrane around the entire perimeter thereof.

4. The process of claim 1 wherein the additional anionic membrane is a membrane having a high degree of croselinking.

5. The process of claim 4 wherein the additional anionic membrane is an ADP membrane.

6. The process of claim 1 wherein the strong organic acid solution is methane sulfonic acid.

7. The process of claim 6 wherein an additional anionic membrane is applied against the anionic face of each one of the bipolar membranes in the repeating series for enhancing the impermeability of each one of the bipolar membranes to salt cation impurities from the respective base compartment and reducing salt cation contamination in the respective acid compartment.

8. The process of claim 6 wherein sealing is provided between the additional anionic membrane and the bipolar membrane around the entire perimeter thereof.

9. The process of claim 6 wherein the additional anionic membrane is a membrane having a high degree of crosslinking.

10. The process of claim 9 wherein the additional anionic membrane is an ADP membrane.

* * * * *

UNITED STATES PATENT AND TRADEMARK OFFICE
CERTIFICATE OF CORRECTION

PATENT NO. : 5,993,629
DATED : November 30, 1999
INVENTOR(S) : Gavach, et al.

It is certified that error appears in the above-identified patent and that said Letters Patent is hereby corrected as shown below:

On the title page, [30] change "Jan. 18, 1996 to --Jan. 19, 1995 --
Claim 1, line 6, change "phospbonic" to --phosphonic--
Claim 1, line 7, change "acide" to --acids--
Claim 4, line 2, change "croselink" to --crosslink--

Signed and Sealed this

Twelfth Day of September, 2000

Attest:

Q. TODD DICKINSON

*Attesting Officer*     *Director of Patents and Trademarks*